United States Patent [19]
Schwab et al.

[11] Patent Number: 6,166,279
[45] Date of Patent: Dec. 26, 2000

[54] PREPARATION OF OLEFINS

[75] Inventors: Peter Schwab, Bad Dürkheim; Ralf Schulz, Speyer; Michael Schulz, Ludwigshafen; Boris Breitscheidel, Limburgerhof; Gerald Meyer, Ludwigshafen, all of Germany

[73] Assignee: BASF Aktiengesellschaft, Ludwigshafen, Germany

[21] Appl. No.: 09/275,784

[22] Filed: Mar. 25, 1999

[30] Foreign Application Priority Data

Mar. 27, 1998 [DE] Germany ............... 198 13 720

[51] Int. Cl.$^7$ .................. C07C 1/00; C07C 6/00
[52] U.S. Cl. ............ 585/324; 585/312; 585/644; 585/646; 585/647
[58] Field of Search .................. 585/324, 312, 585/644, 646, 647

[56] References Cited

U.S. PATENT DOCUMENTS

| | | | |
|---|---|---|---|
| 3,660,506 | 5/1972 | Banks | 260/666 |
| 5,300,718 | 4/1994 | McCaulley | 585/324 |
| 5,698,760 | 12/1997 | Kelly | 585/643 |
| 5,898,091 | 4/1999 | Chodorge et al. | 585/647 |

FOREIGN PATENT DOCUMENTS

| | | |
|---|---|---|
| 2215426 | 3/1998 | Canada . |
| 273817 | 7/1988 | European Pat. Off. . |
| 691318 | 1/1996 | European Pat. Off. . |
| 742195 | 11/1996 | European Pat. Off. . |
| 19640026 | 4/1998 | Germany . |

*Primary Examiner*—Jerry D. Johnson
*Assistant Examiner*—Thuan D. Dang
*Attorney, Agent, or Firm*—Keil & Weinkauf

[57] ABSTRACT

The preparation of olefins from steam cracker or refinery $C_4$ streams is carried out by selective hydrogenation of butadienes and acetylenic impurities in the steam cracker or refinery $C_4$ stream, with simultaneous or subsequent, at least partial isomerization of 1-butene to 2-butene, followed by removal of i-butene from the $C_4$ stream by reaction with an alcohol to form an ether, followed by removal of oxygen-containing impurities from the $C_4$ stream using adsorber materials, followed by two-stage metathesis of the butenes in the $C_4$ stream by conversion of 1-butene and 2-butene present in the $C_4$ stream into propene and 2-pentene and subsequent reaction of the 2-pentene with ethene in the presence of a metathesis catalyst to form propene and 1-butene. Optionally, butadiene may be removed from the $C_4$ stream by extractive distillation in a preliminary step.

17 Claims, 2 Drawing Sheets

FIG.1

FIG.2

PREPARATION OF OLEFINS

FIELD OF THE INVENTION

The present invention relates to a process for preparing olefins, in particular propene from steam cracker or refinery $C_4$ streams in a coupled metathesis process.

Steam crackers are the main source of basic petrochemicals such as ethene, propene, $C_4$-olefins and higher hydrocarbons. In the cracking process, it is necessary to introduce large amounts of energy at high temperatures within a period of time which, on the one hand, is sufficient to carry out cracking but, on the other hand, does not permit further reaction of the cracking products. For this reason, the yield of ethene and propene in the cracking of hydrocarbons is determined essentially by

- the type of hydrocarbons used (naphtha, ethane, LPG, gas oil or the like),
- the cracking temperature
- the residence time
- and the partial pressures of the hydrocarbons.

The highest yield of ethene and propene is achieved at cracking temperatures of from 800 to 850° C. and residence times of from 0.2 to 0.5 s. The main product in this range is always ethene and the $C_3/C_2$ output ratio of from about 0.5 to 0.7 can be increased only slightly by varying the cracking conditions. However, the worldwide demand for propene is increasing more rapidly than that for ethene. A consequence of this is that processes for the downstream utilization of the higher hydrocarbons formed in the cracking process, e.g. $C_4$, with a view to optimizing the propene yield are becoming increasingly important. A tool for this is provided by the metathesis of raffinate II or 2-butene with ethene to form propene. To achieve the necessary composition of the $C_4$ feedstock, the crude $C_4$ stream has to be purified and interfering secondary components have to be removed efficiently.

DESCRIPTION OF THE RELATED ART

Various combination processes for the preparation of propene which include one or more metathesis steps are known. U.S. Pat. No. 5,300,718 describes a process in which a mixed $C_4$ stream comprising 1-butene, 2-butene, isobutene, butadiene and butanes is introduced into an etherification zone in which the isobutene is reacted with an alcohol to form an ether which is separated off from the $C_4$ stream. The stream depleted in isobutene is then brought into contact with a butadiene-selective solvent in order to remove butadiene. The raffinate stream which has in this way been depleted in butadiene is brought into contact with an adsorbing material to remove remaining alcohols and ethers and to form a deoxygenated stream which is subsequently isomerized over an olefin isomerization catalyst to increase the concentration of 2-butene and reduce the concentration of 1-butene. The resulting isomerized stream is subjected together with ethene to a metathesis in the presence of a disproportionation catalyst to form propene.

EP-A-0 742 195 describes a process for converting a $C_4$ fraction into an ether and propene. For this purpose, a crude $C_4$ stream is subjected to a selective hydrogenation of the butadienes and acetylenic impurities with simultaneous isomerization of 1-butene to 2-butene. The isobutene present in the output from the reactor is subsequently reacted with an alcohol in the presence of an acid etherification catalyst and removed as the ether. This is followed by removal of oxygen-containing impurities, after which the 2-butene-rich stream is reacted with ethene in the presence of a metathesis catalyst to form propene.

In the known processes, at least equimolar amounts of ethene are introduced for the preparation of propene.

SUMMARY OF THE INVENTION

It is an object of the present invention to provide a process for preparing olefins, in particular propene as coupled product from steam cracker or refinery $C_4$ streams, which avoids the disadvantages of the known processes.

BRIEF DESCRIPTION OF THE DRAWINGS

The abbreviations used in the figures have the following meanings.

1-Bu: 1-Butene
2-Bu: 2-Butene
Bu: Butanes
Et: Ethene
Pr: Propene
2-Pe: 2-Pentene
3-He: 3-Hexene
H: High boilers
II: Raffinate II
C4: $C_4$-Olefins
C5$^+$: Olefins having 5 or more carbon atoms
R01: Reactor (metathesis)
R02: Reactor (metathesis)
R03: Reactor (isomerization)
K101: Distillation column (preferably a dividing-wall column, side column or 2-column arrangement)
K201: Distillation column (preferably a dividing-wall column, side column or 2column arrangement)
K301: Distillation column

DETAILED DESCRIPTION OF THE INVENTION

We have found that this object is achieved by a process for preparing olefins, in particular propene, from steam cracker or refinery $C_4$ streams by A) if desired, extractive distillation of butadiene from the $C_4$ stream using a butadiene-selective solvent to obtain a substantially butadiene-depleted $C_4$ stream, B) selective hydrogenation of butadienes and acetylenic impurities in the steam cracker or refinery $C_4$ stream or the stream from step A) with simultaneous or subsequent, at least partial isomerization of 1-butene to 2-3-butene in order to obtain a $C_4$ stream which comprises n-butenes and i-butene and is essentially free of butadienes and acetylenic impurities, C) removal of i-butene from the $C_4$ stream obtained in step B) by reaction with an alcohol to form an ether which is separated off and, if desired, redissociated to give pure isobutene, resulting in a $C_4$ stream which comprises n-butenes and possibly oxygen-containing impurities and from which lower- and higher-boiling compounds can also be removed by distillation during the removal of the ether, D) separation of oxygen-containing impurities from the $C_4$ stream obtained in step C) using adsorber materials, E) two-stage metathesis of the butenes in the $C_4$ stream obtained in step D) by a) conversion of the 1-butene and 2-butene present in the $C_4$ stream into propene and 2-pentene in the presence of a metathesis catalyst comprising at least one compound of a metal of transition group VIb, VIIb or VIII of the Periodic Table of the Elements, b) subsequent separation of the propene and 2-pentene formed and the unreacted butenes and, if desired, at least partial discharge of one or more of these compounds, c) subsequent reaction of the 2-pentene with ethene to form propene and 1-butene in the presence of a metathesis catalyst comprising at least one compound of a metal of transition group VIb, VIIb or VIII of the Periodic Table of the Elements, d) subsequent separation of the propene and 1-butene formed, e) if desired, discharge of a pure 1-butene stream and/or, if desired, isomerization of the 1-butene formed to 2-butene in the presence of an isomerization catalyst and subsequent recirculation of the 1-butene which has not been discharged and the 2-butene which may have formed together with part of the $C_4$ fraction which has not been converted in step a) to step a), f) isolation of the propene separated off in steps b) and d), wherein the separation in step d) can be carried out by passing the reacted mixture to step b), wherein, subsequently in step e), the unreacted $C_4$ fraction separated off in step b) is, if desired, at least partly discharged and/or, if desired, the 1-butene present in this $C_4$ fraction is at least partially isomerized to 2-butene in the presence of an isomerization catalyst and the resulting mixture is subsequently recirculated to step a).

The process can be controlled so as to choose as products one or more of the compounds propene, 1-butene, 2-pentene and 3-hexene in step E, butadiene in step A and isobutene or MTBE in step C.

The metathesis reactions carried out in step E are described in DE-A-196 40 026 which has earlier priority but is not a prior publication:

In its simplest form, olefin metathesis (disproportionation) describes the reversible, metal-catalyzed transalkylidenation of olefins by rupture and reformation of C=C double bonds. Here, for example, olefins of the formulae $R^1$—CH=CH—$R^2$ and $R^3$—CH=CH—$R^4$ are converted reversibly into olefins of the formulae $R^1$—CH=CH—$R^3$ and $R^2$—CH=CH—$R^4$. In the metathesis of acyclic olefins, a distinction is made between self-metathesis in which one olefin is converted into a mixture of two olefins having different molar masses and cross-metathesis or cometathesis in which two different olefins react. An example of self-metathesis is the conversion of two molecules of propene into ethene and 2-butene, as is carried out, for example, by the Phillips triolefin process, cf. Hydrocarbon Processing, Volume 46, No. 11, November 1967, p. 232. An example of cross-metathesis is the reaction of propene and 1-butene to give ethene and 2-pentene. If one of the reactants is ethene, the reaction is usually referred to as an ethenolysis.

The metathesis reactions occur in the presence of catalysts. Suitable catalysts are, in principle, homogeneous and heterogeneous transition metal compounds, in particular those of transition groups VI to VIII of the Period Table of the Elements, and also homogeneous and heterogeneous catalyst systems in which these compounds are present.

EP-A1-0 691 318 discloses, for example, an olefin metathesis process in which $C_5$-olefins and ethene are reacted in the presence of a catalyst to give mixed $C_4$-olefins and propene. Thus, 2-methyl-2-butene is reacted with ethene to form isobutene and propene. A mixture of 2-pentenes and 2-methyl-2-butene is converted into a mixture of 1-butene, isobutene and propene.

The process of the present invention encompasses, in step E), 2 metathesis steps. In the first step, 1-butene and 2-butene present in the $C_4$ stream are converted into propene and 2-pentene. In a second step, 2-pentene is then reacted with ethene to form 1-butene and propene. According to one embodiment of the invention, the 1-butene is, if desired, at least partially isomerized in the presence of an isomerization catalyst to form 2-butene and the resulting mixture of 1-butene and 2-butene is recirculated to the first reaction step. By this means, and also by regulation of the conversion over the isomerization catalyst, an optimum ratio of 1-butene to 2-butene can be set at the input of the first metathesis reactor in order to achieve, for example, a maximum yield of propene. The two-stage procedure employing cross-metathesis and ethenolysis enables the raw material requirement of ethene and $C_4$-olefins to be reduced by from about 5 to 15% by weight compared to single-stage ethenolysis processes as are described, for example, in U.S. Pat. No. 3,660,506 and EP-A-0 273 817.

Both metathesis steps can also be configured as a reactive distillation as described below.

In the following, the pretreatment of $C_4$ streams to obtain a $C_4$ stream which can be used in the metathesis is described.

The $C_4$ stream can come, for example, from a cracker, in particular a steam cracker, or a refining step. This $C_4$ stream generally comprises both unsaturated and saturated $C_4$ hydrocarbons. The cracker can be operated as described in the introduction.

The $C_4$ stream is further treated by 1. selective hydrogenation/butadiene extractive distillation of crude $C_4$ fraction to remove 1,3-butadiene, 1,2-butadiene, 1-butyne (ethylacetylene) and butenyne (vinylacetylene), 2. i-butene separation from the resulting raffinate I via etherification with alcohols and 3. purification of the raffinate II stream obtained in this way over adsorber materials to remove oxygen-containing compounds, sulfur compounds, water, chlorides and other secondary components which interfere in the subsequent step, and the above-described 4. metathesis of raffinate II or 2-butene with ethene to give propene.

Selective Hydrogenation of Crude $C_4$ (Step B)

Alkynes, alkynenes and alkadienes are undesirable materials in many industrial syntheses because of their tendency to polymerize or their pronounced tendency to form complexes with transition metals. They sometimes have a very great adverse effect on the catalysts used in these reactions.

The $C_4$ stream from a steam cracker comprises a very high proportion, up to 70% by weight, of multiply unsaturated compounds such as 1,3-butadiene, 1,2-butadiene, 1-butyne (ethylacetylene) and butenyne (vinylacetylene). Depending on the downstream processing carried out, the multiply unsaturated compounds are either extracted (butadiene extractive distillation) or selectively hydrogenated. In the former case, the residual content of multiply unsaturated compounds is typically 0.1–4% by weight while in the latter case it is typically 0.001–0.3% by weight. Since the residual amounts of multiply unsaturated compounds likewise interfere in the further processing, a further removal by selective hydrogenation to values of <10 ppm is necessary. In order to retain the desired butenes, overhydrogenation to butanes should be kept as low as possible. Similar objectives also apply to the treatment of $C_4$ feedstocks from FCC processes (fluid catalytic cracking).

Suitable processes are described, for example, in H. Lauer, Erdöl and Kohle—Erdgas—Petrochemie, 36 (June 1983), 249–251 (cold hydrogenation of unsaturated hydrocarbon streams over noble metal catalysts in a tube reactor) and also in EP-A-0 780 155.

Extraction of Butadiene From Crude $C_4$ (Step A)

All suitable modern processes for isolating butadiene are based on the physical principle of extractive distillation. Addition of selective organic solvents reduces the volatility of specific components of a mixture, in this case butadiene. These therefore remain with the solvent in the bottoms from the distillation column, while the accompanying substances which have previously not been able to be separated off by distillation can be taken off at the top. Solvents employed for the extractive distillation are mainly acetone, furfural, acetonitrile, dimethylacetamide, dimethylformamide (DMF) and N-methylpyrrolidone (NMP). Extractive distillations are particularly suitable for butadiene-rich $C_4$ cracker fractions having a relatively high proportion of alkynes, e.g. methylacetylene, ethylacetylene and vinylacetylene, and methylallene. In modem processes using solvents such as dimethylformamide (Nippon Zeon, Leuna), dimethylacetamide (UCC) or N-methylpyrrolidone (BASF, ABB Lummus Crest), the alkyne separation is a substep in the process flow. The earlier processes, which were developed and employed particularly in the U.S.A., using solvents such as acetone, furfural (Phillips Petroleum) or acetonitrile (Shell, UOP, ARCO) necessitated an upstream partial hydrogenation to avoid troublesome resin formation.

The simplified principle of a solvent extraction from crude $C_4$ fraction can be described as follows: the completely vaporized $C_4$ fraction is fed to an extraction column at its lower end. The solvent (DMF, NMP) flows from the top in countercurrent to the gas mixture and on its way to the bottom is loaded with the more soluble butadiene and small amounts of butenes. At the lower end of the extraction column, part of the pure butadiene obtained is fed in to drive out most of the butenes. The butenes leave the separation column at the top. In a subsequent stripper column, the butadiene is freed of solvent by boiling out and is subsequently purified by distillation. In the preferred NMP process, pure butadiene is obtained in a purity of 99.8%. The butadiene yield is 96%, based on the original content in the crude $C_4$ fraction.

According to the present invention, the output stream from a butadiene extractive distillation is fed to the second stage of a selective hydrogenation in order to reduce the residual butadiene content to values of <10 ppm.

The $C_4$ stream remaining after separation of butadiene is referred to as $C_4$ raffinate or raffinate I and comprises mainly the components i-butene, 1-butene, 2-butenes and n- and i-butane.

Separation and Isolation of i-butene From Raffinate I (Step C)

In the further fractionation of the $C_4$ stream, i-butene is subsequently removed extractively by reaction with alcohols over acid ion exchangers. Preference is given to using methanol (gives MTBE) or i-butanol (gives IBTBE) for this purpose.

The preparation of MTBE from methanol and i-butene is carried out at 30–100° C. and a slightly superatmospheric pressure in the liquid phase over acid ion exchangers. The reaction is carried out either in two reactors or in a two-stage shaft reactor in order to achieve virtually complete i-butene conversion (>99%). The pressure-dependent formation of a methanol/MTBE azeotrope means that the isolation of pure MTBE requires a multistage pressure distillation or is achieved by more recent technology (Erdölchemie/Bayer) by methanol adsorption on adsorber resins. All other components of the $C_4$ fraction remain unaltered. Small amounts of diolefins and acetylenes shorten the life of the ion exchanger due to polymer formation. New developments have led to a bifunctional Pd-containing ion exchanger over which only diolefins and acetylenes are hydrogenated in the presence of small amounts of hydrogen. The etherification of the i-butene remains unaffected by this. MTBE is used primarily for increasing the octane number of gasoline.

The etherification of i-butene with i-butanol to give IBTBE is, according to EP-B-0 003 305 and EP-B-0 015 513, carried out over an acid ion exchanger. The reaction is preferably carried out in a reactor cascade comprising three approximately adiabatically operated fixed-bed reactors with intermediate cooling at pressures of 8–20 bar. The main conversion occurs in the first reactor (80–90%) and the completion of the conversion to the equilibrium conversion, which is 98–99% at high pressures and low temperatures, is achieved in the remaining stages. In the downstream column, raffinate II is taken off as a side stream, leaving unreacted i-butene (spec. <3%). IBTBE and higher-boiling materials are taken off at the bottom.

IBTBE and MTBE can be redissociated in the gas phase at 150–300° C. over acid oxides for the purpose of isolating pure i-butene. For this purpose, for example, the bottoms consisting predominantly of IBTBE are vaporized and redissociated into i-butene and i-butanol over an acid catalyst. In the subsequent separation sequence, pure i-butene is taken off at the top.

The advantage of the IBTBE process over the MTBE process for the purposes of the process of the present invention is that there is no formation of highly volatile oxygen-containing compounds such as dimethyl ether which cannot be separated off sufficiently in distillative work-up of the etherification product and represent strong catalyst poisons in the subsequent metathesis reaction.

Feed Purification of the Raffinate II Stream Over Adsorber Materials (Step D)

To improve the operating life of the catalysts used in the subsequent metathesis step, the use of a feed purification step (guard bed) for removing catalyst poisons such as water, oxygen-containing compounds, sulfur or sulfur compounds or organic halides is necessary.

Suitable processes for adsorption and adsorptive purification are described, for example, in W. Kast, Adsorption aus der Gasphase, VCH, Weinheim (1988). The use of zeolitic adsorbents is explained in D. W. Breck, Zeolite Molecular Sieves, Wiley, N.Y. (1974).

The process sequence described for utilizing $C_4$ fraction from steam crackers or FCCs to produce propene makes it possible to achieve better economics in respect of the utilization of the starting materials crude $C_4$ and ethene compared to conventional processes.

In the following, the individual process steps of the preferred embodiment are described in greater detail.

Selective Hydrogenation of Crude $C_4$ Fraction (Step B)

The crude $C_4$ fraction from a steam cracker or a refinery is first subjected to a two-stage selective hydrogenation of butadiene (1,2- and 1,3-butadiene) and alkynes or alkenynes present in the $C_4$. In one embodiment, the $C_4$ stream from a refinery can also be fed directly into the second step of the selective hydrogenation. The first step of the hydrogenation is preferably carried out over a catalyst comprising from 0.1 to 0.5% by weight of palladium on aluminum oxide as support. The reaction is carried out in the gas/liquid phase in a fixed bed (downflow mode) with a liquid circuit. The hydrogenation is carried out at from 40 to 80° C. and a pressure of from 10 to 30 bar, a molar ratio of hydrogen to butadiene of from 10 to 50 and a liquid hourly space velocity (LHSV) of up to 15 m³ of fresh feed per m³ of catalyst per hour and a ratio of recycle to input stream of from 5 to 20.

The second step of the hydrogenation is preferably carried out over a catalyst comprising from 0.1 to 0.5% by weight of palladium on aluminum oxide as support. The reaction is carried out in the gas/liquid phase in a fixed bed (downflow mode) with a liquid circuit. The hydrogenation is carried out at from 50 to 90° C. and a pressure of from 10 to 30 bar, a molar ratio of hydrogen to butadiene of from 1.0 to 10 and a liquid hourly space velocity (LHSV) of from 5 to 20 m³ of fresh feed per m³ of catalyst per hour and a ratio of recycle to input stream of from 0 to 15.

The hydrogenation is preferably carried out under low to medium isomerization conditions for butene, in particular for 1-butene to 2-butene. The residual butadiene content can be from 1 to 100 ppm depending on the intensity of the hydrogenation.

The reaction product obtained in this way is referred to as raffinate I and comprises i-butene and n/i-butane plus 1-butene and 2-butene in an optimum molar ratio for the metathesis.

Alternatively: Separation of Butadiene From Crude $C_4$ Fraction by Extractive Distillation (Step A)

Butadiene is separated from crude $C_4$ fraction by extractive distillation using N-methylpyrrolidone.

The output stream from the extractive distillation is, according to one embodiment of the invention, fed to the second step of the above-described selective hydrogenation in order to remove residual amounts of butadiene and to set the desired molar ratio of 1-butene to 2-butene.

Removal of i-butene Via Etherification With Alcohols (Step C)

In the etherification step, i-butene is reacted with alcohols, preferably with i-butanol, over an acid catalyst, preferably an acid ion exchanger, to form ethers, preferably i-butyl tert-butyl ether. In one embodiment of the invention, the reaction is carried out in a three-stage reactor cascade in which the etherification stream flows from the top downward through flooded fixed-bed catalysts. In the first reactor, the inlet temperature is from 0 to 60° C., preferably from 10 to 50° C., the outlet temperature is from 25 to 85° C., preferably from 35 to 75° C., and the pressure is from 2 to 50 bar, preferably from 3 to 20 bar. At a ratio of i-butanol to i-butene of from 0.8 to 2.0, preferably from 1.0 to 1.5, the conversion is from 70 to 90%.

In the second reactor, the inlet temperature is from 0 to 60° C., preferably from 10 to 50° C., the outlet temperature is from 25 to 85° C., preferably from 35 to 75° C., and the pressure is from 2 to 50 bar, preferably from 3 to 20 bar. The total conversion over the two stages is increased to from 85 to 99%, preferably from 90 to 97%.

In the third and largest reactor, the equilibrium conversion is achieved at identical inlet and outlet temperatures of from 0 to 60° C., preferably from 10 to 50° C.

The etherification and separation of the ether formed is followed by ether dissociation in order to obtain isobutene in high purity. The endothermic reaction is carried out over acid catalysts, preferably over acid heterogeneous catalysts, for example phosphoric acid on an $SiO_2$ support, at an inlet temperature of from 150 to 300° C., preferably from 200 to 250° C., and an outlet temperature of from 100 to 250° C., preferably from 130 to 220° C.

When using a $C_4$ fraction from FCC, it has to be expected that propane, i-butane and other hydrocarbons which can adversely affect the subsequent process sequence may be introduced in relatively large amounts. Accordingly, the possibility of removing these components by distillation is provided for in the work-up of the ether.

The resulting output stream is referred to as raffinate II and has a residual i-butene content of from 0.1 to 3% by weight.

Purification of the Raffinate II Stream Over Adsorber Materials (Step D)

The raffinate II stream obtained after the etherification (and distillation) is purified over at least one guard bed comprising high surface area aluminum oxides, silica gels, aluminosilicates or molecular sieves. The guard bed serves to dry the $C_4$ stream and to remove substances which can act as catalyst poisons in the subsequent metathesis step. The purification is carried out in drying towers, preferably at temperatures and pressures which are selected so that all components are present in the liquid phase. If desired, the purification step is used for preheating the feed for the subsequent metathesis step.

The raffinate II stream after this step is virtually free of water, oxygen-containing compounds, organic chlorides and sulfur compounds. When the etherification step is carried out using methanol to prepare MTBE, it may be necessary, owing to the formation of dimethyl ether as secondary component, to combine or carry out in succession a plurality of purification steps, which is not necessary when i-butene is separated off via IBTBE.

Two-Stage Metathesis Reaction for Preparing Propene (Step F)

The resulting raffinate II stream, which comprises 1-butene, 2-butenes and butanes, can, for example, comprise from 70 to 90% by weight of olefins and from 10 to 30% by weight of butanes, with, for example, from 25 to 50% by weight of 1-butene, from 30 to 55% by weight of 2-butene and not more than from 1 to 2% by weight of isobutene. According to one embodiment of the invention, the $C_4$ stream can also contain small amounts of other hydrocarbons.

Apart from the conversion of 1-butene and 2-butene into propene and 2-pentene, a small proportion of 3-hexene and ethene can be obtained as by-product in the metathesis. In addition, small amounts of higher-boiling compounds can also be present.

The small amounts of by-products which, according to one embodiment of the invention, make up from 1 to 30% by weight, preferably from 5 to 20% by weight, based on the amounts of 2-pentene formed, do not interfere in the subsequent reaction. According to one embodiment of the invention, 2-pentene and 3-hexene can be obtained as products.

Thus, the expression "2-pentene" also includes mixtures which comprise not only 2-pentene but also small amounts of hexenes, in particular 3-hexene, and other higher-boiling compounds. Correspondingly, the expression "butenes", for example "1-butene" and "2-butene", also includes a mixture comprising not only the butene or the butenes but also $C_4$-alkanes, in particular butanes.

In the first metathesis step, raffinate II is reacted over a heterogeneous disproportionation catalyst, preferably a rhenium oxide on aluminum oxide. The catalyst is obtained by impregnation of the support with aqueous ammonium perrhenate or perrhenic acid solution or by spraying-on of the solutions, subsequent drying and calcination. The reaction is carried out at from 0° C. to 100° C., preferably at from 20 to 90° C., and a pressure which is at least slightly higher than the vapor pressure of the $C_4$ components in the feed. The reaction is carried out in tube reactors or shaft ovens in a synthesis/regeneration cycle mode.

In this first metathesis step, propene and 2-pentene are formed from 1-butene and 2-butene in the main reaction and ethene and 3-hexene are formed in a secondary reaction. The reaction is carried out so that the output ratio of propene to 2-pentene is maximized. The total $C_4$ conversion in this step is from 30 to 70%, preferably from 40 to 65%.

The output stream from the reaction subsequently goes through a distillation step: the pressure column used for this purpose can be configured as a dividing-wall column, side column, side-offtake column or two-column arrangement and serves to separate the reaction mixture into a $C_2/C_3$ low boiler phase, a $C_4$ intermediate boiler phase and a $C_5/C_6$ high boiler phase. Pressures and temperatures in the column are set so as to correspond to the specified separation task. Any higher-boiling components formed can be discharged in the bottoms from the column.

In the second metathesis step, at least some of the $C_5/C_6$ high boiler fraction obtained in the above-described distillation is reacted with ethene over a heterogeneous disproportionation catalyst, preferably a rhenium oxide on aluminum oxide. The catalyst is obtained by impregnation of the support with aqueous ammonium perrhenate or perrhenic acid solution or by spraying-on of the solutions, subsequent drying and calcination. The reaction is carried out at from 0° C. to 100° C., preferably from 20 to 90° C., and a pressure which is at least slightly higher than the vapor pressure of the components of the feed. The pressure is preferably from 30 to 70 bar. This reaction, too, is carried out in tube reactors or shaft ovens in a synthesis/regeneration cycle mode.

In this second metathesis step, propene and 1-butene are formed from the $C_5/C_6$ high boiler fraction comprising the olefins 2-pentene and 3-hexene when feeding-in ethene, with the molar ratio of $C_2:C_5/C_6$ being from 0.5 to 5, preferably from 0.8 to 2.0. The total conversion in this step is from 30 to 95%, preferably from 50 to 80%. The output stream from the second metathesis step is likewise fed to the above-described distillation column for separating the reaction mixture into a $C_2/C_3$ low boiler phase, a $C_4$ intermediate boiler phase and a $C_5/C_6$ high boiler phase. Any higher-boiling components formed can be discharged in the bottoms from the column.

The $C_2/C_3$ low boiler fraction from the columns is passed to a further distillation column in which the fine distillation of propene occurs. At least some of the ethene which is separated off is recirculated to the second metathesis step.

At least some of the $C_4$ intermediate boiler fraction from the column is recirculated to the first metathesis step. Fresh $C_4$ feed and $C_4$ recycle stream are combined in such amounts that the first metathesis step is provided with a feed stream which has a 1-butene to 2-butene molar ratio of from 5:1 to 1:5.

Figure 1:
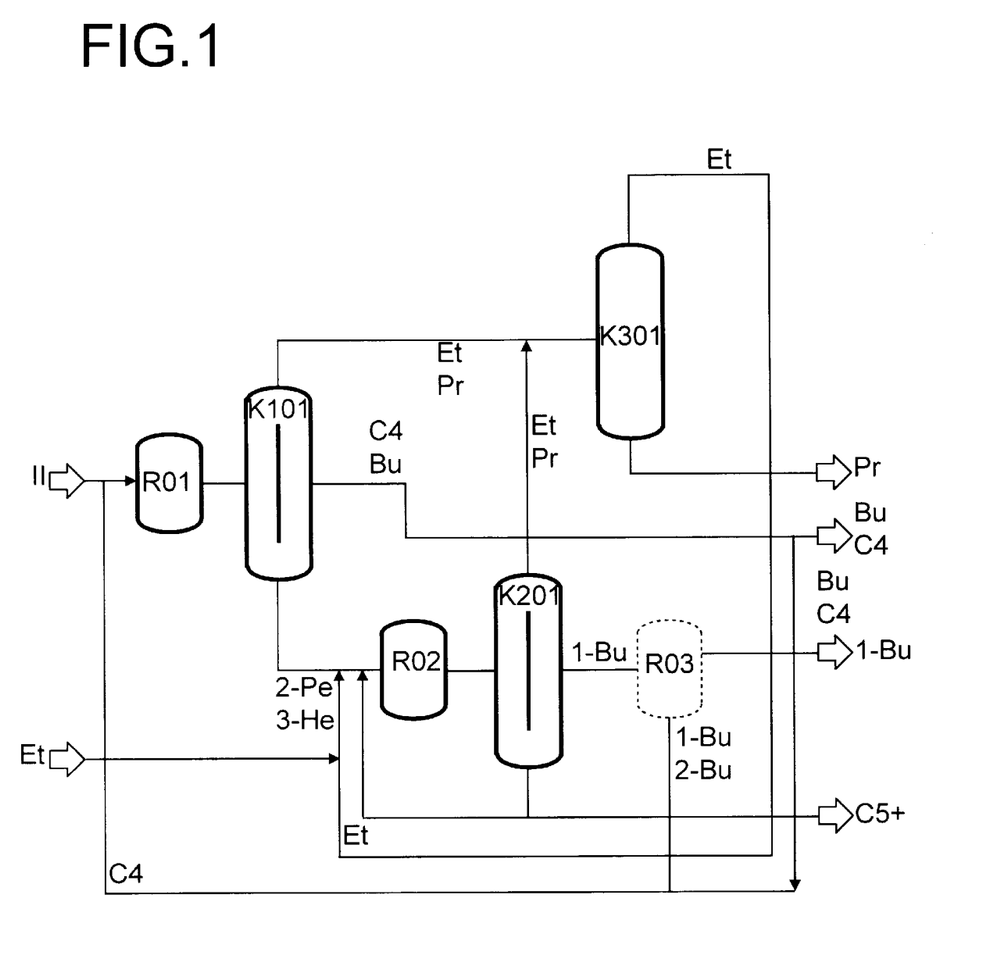
FIG. 1 schematically shows an embodiment of process step E described below to the present invention.

Some embodiments of step E of the invention are described below with the aid of the drawing in which A preferred embodiment of process step E according to the present invention, as shown in FIG. 1, is described below.

In a first reactor R01, 1-butene and 2-butene are reacted in the presence of the metathesis catalyst according to the present invention to form propene and 2-pentene. For this purpose, a raffinate II stream is fed to the reactor. The reactor is followed by a distillation column K101 configured as a dividing-wall column, side column or 2-column arrangement and propene and ethene formed as by-product are taken off at the top of this distillation column K101. Unreacted raffinate II is taken off at the middle offtake and is partly recirculated to the feed stream of raffinate II. Some of it can also be discharged. 2-Pentene and 3-hexene formed as by-product as well as high boilers are taken off at the bottom of K101. The bottoms are then fed together with introduced ethene to a reactor R02 which again contains a metathesis catalyst according to the present invention. In this reactor R02, the reaction of 2-pentene with ethene to form 1-butene and propene takes place. The output from reactor R02 is fed to a distillation column K201 configured as a dividing-wall column, side column or 2-column arrangement and propene and unreacted ethene are taken off at the top of this distillation column K201. At the middle offtake, 1-butene formed is, if desired, partly discharged and, if desired, at least some of it is fed to the isomerization reactor R03. Unreacted 2-pentene as well as 3-hexene and high boilers as by-products are obtained in the bottoms from K201. These are discharged or preferably recirculated to R02. The mixtures of propene and by-product ethene taken off at the top of K101 and K201 are separated in a further distillation column K301. Ethene is obtained at the top of K301 and is preferably (re)circulated to the reactor R02. In the isomerization reactor R03, the 1-butene is at least partly isomerized to 2-butene over an isomerization catalyst and the isomerization mixture is recirculated to the reactor R01. The broken line in R03 indicates the possible discharge of the 1-butene. The propene obtained in the bottoms from K301 is, apart from any 1-butene discharged from K201, the desired reaction product of the process of the present invention. K101 and K201 are designed such that a low-boiling phase, in particular a $C_2/C_3$ phase comprising ethene and propene, is taken off at the top of the column. $C_4$ streams are taken off as intermediate-boiling phase, in particular butenes and butanes. $C_{\geq 5}$-hydrocarbons are obtained as bottoms. Between the steps b) and c), the 2-pentene- and 3-hexene-containing high boiler stream which is separated off can be subjected to a distillation to separate 2-pentene and 3-hexene. The distillation can be carried out in any suitable apparatus. The 2-pentene-containing fraction is then fed to the reactor R02. The 2-pentene and/or 3-hexene can be discharged and, for example, passed to a dimerization to produce a $C_{10}$- or $C_{12}$-olefin mixture.

The reactors R01, R02 and R03 can be any reactors which are suitable for continuous operation. According to one embodiment, the reactors can be tube reactors or reaction columns. Preference is given to tube reactors.

The distillation columns K101 and K201 are, according to one embodiment of the invention, columns which allow fractionation of a hydrocarbon stream into $C_2/C_3$ streams, $C_4$ streams and $C_{\geq 5}$ streams. The columns can be configured as dividing-wall columns, side columns or as 2-column arrangements. According to one embodiment of the invention, K301 is a column which allows the separation of ethene and propene. According to an embodiment of the invention, the reactor R01 is combined with the distillation column K101 to form a reactive distillation unit. Here, the reaction is carried out directly in the distillation column. The catalyst is present in the reaction column so that the distillation is carried out simultaneously with the reaction or immediately thereafter. Such a process is known as "reactive distillation".

According to one embodiment, reactor R02 and distillation column K201 are combined to form a reactive distillation unit in which reaction and distillation are combined to form a reactive distillation apparatus in which reaction and distillation are combined as in the above-described reactive distillation.

According to one embodiment of the invention, both reactions take place in reactive distillation apparatuses. Both reactions are equilibrium reactions so that, according to one embodiment of the invention, the process products are removed as quickly as possible from the equilibrium so as to achieve as high as possible a yield. This is, in particular, possible when using reactive distillation apparatuses.

Figure 2:
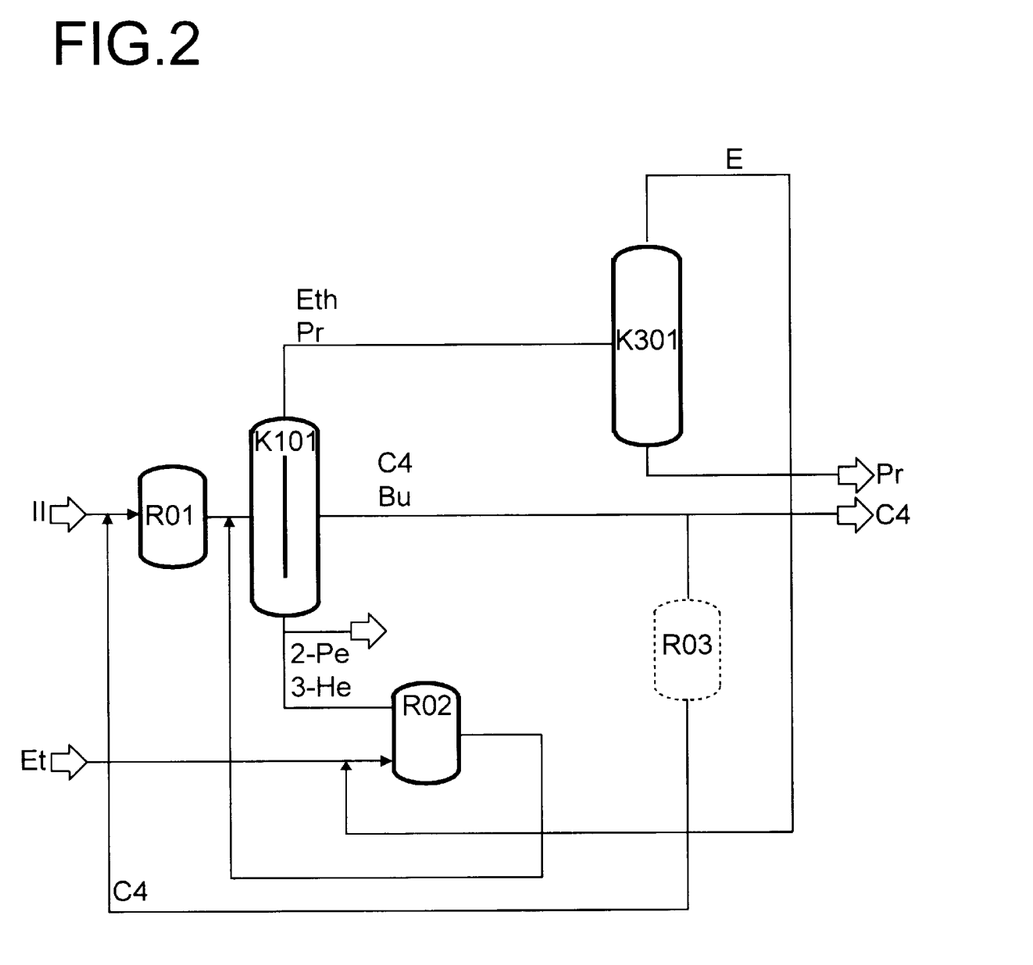
FIG. 2 schematically shows a further embodiment of process step E according to the present invention.

A further embodiment of the process step F of the present invention is shown in FIG. 2.

The mixture obtained from the second metathesis reactor R02 is returned directly to the distillation column K101. The intermediate boiler stream comprising $C_4$-olefins and butanes obtained from column K101 is, if desired, at least partly discharged and/or, if desired, at least partly reacted in the isomerization reactor R03 in which 1-butene is isomerized to 2-butene. The output from the isomerization reactor R03 is recirculated to step a), i.e. the metathesis reactor R01. In this process variant, the distillation column K201 can be omitted.

METATHESIS CATALYST

In the process of the present invention, all suitable metathesis catalysts can be used in R01 and R02.

According to one embodiment of the invention, the catalyst is a heterogeneous catalyst, in particular a supported catalyst. According to one embodiment of the invention, the catalyst comprises at least one compound of a metal of transition group VIb, VIIb or VIII of the Periodic Table of the Elements. The catalyst preferably comprises a rhenium compound. Such catalysts are described, for example, in K. J. Ivin, I. C. Mol, Olefin Metathesis and Metathesis Polymerization, 2nd Edition, Academic Press, New York, 1996; G. W. Parshall, S. D. Ittel, Homogeneous Catalysis, 2nd Edition, 1992, John Wiley & Sons, New York, Chichester, Brisbane, Toronto, Singapore, p. 217ff; R. H. Grubbs in Prog. Inorg. Chem., S. Lippard (editor), John Wiley & Sons, New York, 1978, Vol. 24, 1–50; R. H. Grubbs in Comprehensive Organomet. Chemie., G. Wilkinson (editor), Pergamon Press, Ltd., New York, 1982, Vol. 8, 499–551; D. S. Breslow, Prog. Polym. Sci. 1993, Vol. 18, 1141–1195.

According to an embodiment of the invention, the metal compound is a metal oxide, partial oxide with additional organic radicals or a carbonyl compound.

The metal compound is preferably an oxide of rhenium, in particular $Re_2O_7$.

SUPPORT

According to an embodiment of the invention, the catalysts used according to the invention comprise a support. Supports employed are, in particular, inorganic supports such as $Al_2O_3$, in particular $\gamma$-$Al_2O_3$, $SiO_2$, $Fe_2O_3$, or mixtures thereof such as $SiO_2/Al_2O_3$, $B_2O_3/SiO_2/Al_2O_3$ or $Fe_2O_3/Al_2O_3$.

The metal oxide content on the support is, according to one embodiment of the invention, from 1 to 20% by weight, preferably from 3 to 15% by weight, in particular from 8 to 12% by weight, based on the total weight of the supported catalyst.

The catalyst used is preferably $Re_2O_7$ on $Al_2O_3$, $SiO_2/Al_2O_3$, $SiO_2/Al_2O_3/Fe_2O_3$ or $B_2O_3/Al_2O_3$. Here, the proportion of metal oxide is preferably from 1 to 20% by weight, particularly preferably from 3 to 10% by weight. According to one embodiment of the invention, $MeReO_3$ is used in place of $Re_2O_7$ or in admixture therewith.

According to the present invention, particular preference is given to using $Re_2O_7$ on $Al_2O_3$.

The catalysts are, in one embodiment of the invention, used freshly calcined, in which case they require no further activation, for example by means of alkylating agents. Deactivated catalysts can, according to the invention, be regenerated by burning off coke residues, for example at 550° C. in a stream of air, and cooling under inert gas.

The reactions according to the present invention can be carried out in the presence of a solvent, for example a hydrocarbon solvent. According to a preferred embodiment of the invention, the reactions are carried out without a further added solvent.

ISOMERIZATION CATALYST

As isomerization catalyst, it is possible to use all catalysts which catalyze the isomerization of 1-butene to 2-butene. Suitable isomerization catalysts are, in principle, all homogeneous or heterogeneous noble metal compounds, in the presence or absence of hydrogen, as described, for example, in A. J. Hubert, H. Reimbinger, Synthesis 1970,1,405.

For example, the isomerization can be carried out as described in U.S. Pat. No. 3,592,868 over $RuO_3$ on an inorganic support such as $SiO_2$, $Al_2O_3$ or $TiO_2$ or mixed supports. U.S. Pat. No. 4,684,760 and U.S. Pat. No. 4,889,840 describe mixed catalysts comprising magnesium oxide, zirconium oxide and an alkali metal oxide on an inorganic support. EP-A-0 129 899 and DE-A-34 27 979 describe suitable phosphoric acids and phosphate-containing compounds and also zeolites of the pentasil type or zeolites doped with transition metals. The zeolites of the ZSM type, e.g. ZSM-22, ZSM-23 and ZSM-35, described in U.S. Pat. No. 5,177,281 are advantageous in terms of catalyst life and reaction conditions. Particularly active palladium catalysts, for example on $Al_2O_3$ as support, are described in U.S. Pat. No. 3,531,545.

The isomerization catalyst is preferably a heterogeneous catalyst comprising a compound of a noble metal selected from among the transition elements of the Periodic Table of the Elements; this noble metal may be present in the form of the metal or an oxide or mixed oxide. Also suitable are compounds of a metal of main group I or II of the Periodic Table of the Elements, which can be present as oxide or mixed oxide.

The isomerization catalyst used is preferably a metal or metal oxide of transition group VII or VIII of the Periodic Table of the Elements which may be present on a support, in an inert gas atmosphere or in the presence of hydrogen.

The preferred alkali metal oxide and/or alkaline earth metal oxide catalysts to be used according to the present invention are preferably prepared by impregnation of inorganic supports such as $SiO_2$, $Al_2O_3$, $ZrO_2$, $TiO_2$ or mixtures thereof with alkali metal compounds and/or alkaline earth metal compounds, subsequent drying and calcination to give the corresponding oxides. Deactivated catalyst can be readily regenerated by burning off coke residues at above 350° C. in a stream of air and cooling in an inert gas atmosphere.

The isomerization catalyst used is particularly preferably PdO on an $Al_2O_3$ or $SiO_2$ support in the presence of hydrogen; here, the Pd content is from 0.1 to 5% by weight, based on the total weight of the catalyst.

When using the abovementioned catalysts, the $C_4$ intermediate boiler fraction from the column K201 is partially isomerized to convert it into a mixture of 1-butene and 2-butenes and recirculated to the cross-metathesis in R01 to increase the propene yield. Alternatively, if the raffinate II feed stream is sufficiently pure, 1-butene can be isolated without further work-up. It can then be used, for example, for preparing polymers such as LLDPE copolymers, HDPE copolymers, poly-1-butene or for the preparation of butylene oxide.

In the isomerization, just as in the metathesis reactions in R01 and R02, the conditions are selected such that the reactants are present in the liquid phase. The temperature is thus preferably from 0 to 200° C., particularly preferably from 50 to 150° C. The pressure is preferably from 2 to 200 bar. The isomerization is preferably completed after from one second to one hour, preferably from 5 to 30 minutes. It can be carried out continuously or batchwise and the reactors can be, like the metathesis reactors, glass pressure vessels, tube reactors or distillation columns. Here too, preference is given to using tube reactors.

The invention is illustrated below by means of examples.

EXAMPLES

Example 1
Continuous Experiment on the Two-Stage Selective Hydrogenation of Crude $C_4$ Fraction Crude $C_4$ fraction having a composition of 43.7% of butadiene (including butenyne and butyne), 14.3% of 1-butene, 7.8% of 2-butenes and 7.2% of n-butane was reacted with 175 standard l/h of hydrogen in a continuous-flow tube reactor over a 0.3% $Pd/Al_2O_3$ heterogeneous catalyst at an LHSV of 9.0 $h^{-1}$ at a reactor inlet temperature of 20° C., using a fresh input of 1 kg/h of crude $C_4$ and a circulation of 8.2 kg/h. In the first stage of the selective hydrogenation under these conditions, a total butene selectivity of 99.6% and a 1-butene selectivity of 56.5% were achieved at a butadiene conversion of 95.2%.

A typical output stream from the first stage of the selective hydrogenation, comprising 0.61% of butadiene (including butenyne and butyne), 26.9% of 1-butene, 14.9% of 2-butenes and 11.6% of n-butane, was reacted with 16 standard l/h of hydrogen in a continuous-flow tube reactor over a 0.3% $Pd/Al_2O_3$ s heterogeneous catalyst at an LHSV of 20 $h^{-1}$ at a reactor inlet temperature of 60° C. and a reactor outlet temperature of 70° C., using a fresh input of 2.2 kg/h of reactor output from the first stage and a circulation of 4.0 kg/h. Under these conditions, a raffinate I stream having a residual content of 48 ppm of butadiene was obtained at a butadiene conversion of 99.2% and a 1-butene yield of 58.2%.

Example 2
Continuous Experiment on the Separation of i-butene by Etherification With i-butanol In a three-stage reactor cascade, raffinate I and i-butanol were passed from the top downward through a flooded fixed bed comprising an acid ion exchanger, with the ratio of i-butanol to i-butene in the feed being set to 1.2. The reactor inlet temperature was 40° C., the reactor outlet temperature was 65° C. and the reaction pressure was 8 bar. The measured i-butene conversion after the first stage was 85%.

In the second, similarly dimensioned reactor, the conversion was increased to 95% at a reactor inlet temperature of 40° C., a reactor outlet temperature of 50° C. and a reaction pressure of 8 bar.

In the third, significantly larger reactor, the conversion was brought to the equilibrium value at a reactor inlet temperature and reactor outlet temperature of 40° C. in each case and a reaction pressure of 8 bar. The remaining raffinate stream obtained under these conditions after separating off i-butyl tert-butyl ether by distillation had a residual i-butene content of 0.7% which did not adversely affect the subsequent metathesis step.

Example 3
Continuous Experiment on the Two-Stage Metathesis of Raffinate II

A raffinate stream obtained as described in Example 2 (1.05 kg/h, n-butene content=85%) was mixed with $C_4$ recycle (2.82 kg, n-butene content=55%) and, after feed purification over molecular sieve 13X, passed continuously at 40° C. and 10 bar through a tube reactor charged with an $Re_2O_7/Al_2O_3$ heterogeneous catalyst. The output from the reactor was passed to a pressure distillation (20 bar) in which a $C_2/C_3$ low boiler phase consisting of 83% of propene and 17% of ethene, which were subsequently finely distilled, an intermediate boiler fraction comprising $C_4$-olefins and butanes, of which 10% was discharged, and a high boiler fraction comprising 2-pentene and 3-hexene were separated. The latter was, after partial discharge of $C_5$-hydrocarbons, reacted with 0.5 kg/h of ethene in the ethenolysis reaction which was carried out continuously at 40° C., 35 bar of ethene in a tube reactor charged with an $Re_2O_7/Al_2O_3$ heterogeneous catalyst to give an ethenolysis output stream comprising propene and 1-butene and having a propene content of 22% by weight. The ethenolysis output stream was likewise fed to the pressure distillation.

We claim:

1. A process for preparing olefins from steam cracker or refinery C streams which comprises:

A) optionally extractively distilling butadiene from the $C_4$ stream using a butadiene-selective solvent to obtain a substantially butadiene-depleted $C_4$ stream, B) selectively hydrogenating butadienes and acetylenic impurities in the steam cracker or refinery $C_4$ stream or the stream from step A) with simultaneous or subsequent, at least partial isomerization of 1-butene to 2-butene in order to obtain a $C_4$ stream which comprises n-butenes and i-butene and is essentially free of butadienes and acetylenic impurities, C) removing i-butene from the $C_4$ stream obtained in step B) by reaction with an alcohol to form an ether which is separated off and, optionally, redissociated to give pure isobutene, resulting in a $C_4$ stream which comprises n-butenes and, optionally, removing compounds which are lower boiling than the $C_4$ stream and/or compounds which are higher boiling than the $C_4$ stream by distillation during the removal of the ether, D) separating oxygen-containing impurities from the $C_4$ stream obtained in step C) Using adsorber materials, E) performing a two-stage metathesis of the butenes in the $C_4$ stream obtained in step D) by a) conversion of the 1-butene and 2-butene present in the $C_4$ stream into propene and 2-pentene in the presence of a metathesis catalyst comprising at least one compound of a metal of transition group VIb, VIIb or VIII of the Periodic Table of the Elements, b) subsequent separation of the propene and 2-pentene formed and the unreacted butenes and, optionally, at least partial discharge of one or more of these compounds, c) subsequent reaction of the 2-pentene with ethene to form propene and 1-butene in the presence of a metathesis catalyst comprising at least one compound of a metal of transition group VIb, VIIb or VIII of the Periodic Table of the Elements, d) subsequent separation of the propene and 1-butene formed, e) optionally, at least partial discharge of a pure 1-butene stream and/or at least partial isomerization of the 1-butene formed to 2-butene in the present of an isomerization catalyst and subsequent recirculation of the 1-butene which has not been discharged and any 2-butene which was formed together with part of the $C_4$ fraction which has not been converted in step a) back to step a), f) isolation of the propene separated off in steps b) and d).

2. A process as claimed in claim 1, wherein step E b)and/or step E d) is a distillation.

3. A process as claimed in claim 1, wherein the reaction in steps E a) and/or E c) is not complete and a $C_2/C_3$ low boiler phase, a $C_4$ intermediate boiler phase and a $C_{\geq 5}$ bottom phase are obtained in step E b) and/or E d), where the, optionally combined, low boiler phases are separated into $C_2$ and $C_3$ phases by distillation and the $C_2$ phase is recirculated to step E c), the, optionally combined, intermediate boiler phases are at least partly recirculated to step E a) and the, optionally combined, bottom phases are at least partly recirculated to step c).

4. A process as claimed in claim 1, wherein, when optional step A) is carried out, step B is carried out in one stage, and when optional step A) is not carried out, step B is carried out in two stages, with simultaneous isomerization of 1-butene to 2-butene by bringing the $C_4$ stream in the liquid phase into contact with a catalyst comprising at least one metal selected from the group consisting of nickel, palladium and platinum on a support, at from 20 to 200° C., a pressure of from 1 to 50 bar, a space velocity of from 0.5 to 30 m³ of fresh feed per m³ of catalyst per hour and a ratio of recycle to input stream of from 0 to 30 at a molar ratio of hydrogen to diolefins of from 0.5 to 50, in order to obtain a $C_4$ stream.

5. A process as claimed in claim 1, wherein step A) is carried out, and said butadiene-selective solvent is selected from the class consisting of polar aprotic solvents.

6. A process as claimed in claim 1, wherein the etherification of i-butene in step C) is carried out in a reactor cascade and said alcohol is methanol or i-butanol, in the presence of an acid catalyst, where the reaction mixture flows from the top downward through flooded fixed-bed catalysts in the reactor cascade and the reactor inlet temperature is from 0 to 60° C., the outlet temperature is from 25 to 85° C., the pressure is from 2 to 50 bar, the ratio of i-butanol to i-butene is from 0.8 to 2.0, and the total conversion corresponds to the equilibrium conversion.

7. A process as claimed in claim 1, wherein step D) is carried out over at least one guard bed comprising said adsorber materials, which are selected from the group consisting of high surface area aluminum oxides, silica gels, aluminosilicates and/or molecular sieves.

8. A process as claimed in claim 1, wherein step E) is carried out using a heterogeneous metathesis catalyst comprising a rhenium compound, on an inorganic support.

9. A process as claimed in claim 5, wherein said polar aprotic solvent is selected from the group consisting of acetone, furfural, acetonitrile, dimethylacetamide, dimethylformamide and N-methyl-pyrrolidone.

10. A process as claimed in claim 4, wherein said catalyst is palladium on aluminum oxide.

11. A process as claimed in claim 6, wherein said alcohol is i-butanol.

12. A process as claimed in claim 6, wherein said acid catalyst is an acid ion exchanger.

13. A process as claimed in claim 7, wherein step D) results in preheating of the feed for the subsequent metathesis step.

14. A process as claimed in claim 8, wherein said catalyst is rhenium oxide.

15. A process as claimed in claim 1, wherein said separation in step E d) is carried out by passing the unreacted mixture to step E b), and subsequently in step E e) the unreacted $C_4$ fraction separated off in step b) is at least partly discharged, and the 1-butene present in that $C_4$ fraction is at least partially isomerized to 2-butene in the presence of an isomerization catalyst and the resulting mixture is subsequently recirculated to step E a).

16. A process as claimed in claim 6, wherein said reactor cascade has an inlet temperature of from 10 to 50° C., an outlet temperature of from 35 to 75° C., the pressure is from 3 to 20 bar, and the ratio of i-butanol to i-butene is from 1.0 to 1.5.

17. A process as claimed in claim 2, wherein either or both of said distillations are carried in a dividing-wall column, side column or 2-column arrangement, and a propene-containing low boiler phase, a butene-containing intermediate boiler phase and a 2-pentene-containing bottom phase are obtained.

* * * * *